United States Patent [19]

Boyer

[11] Patent Number: 5,028,704

[45] Date of Patent: Jul. 2, 1991

[54] (2,5-DIHYDRO 5-PHENYL-2-OXO-3-FURANYL)AMINES, METHODS OF MANUFACTURE, AND USE THEREOF IN THE PRODUCTION OF ANGIOTENSIN CONVERTING ENZYME INHIBITORS

[75] Inventor: Stephen K. Boyer, Lebanon, N.J.

[73] Assignee: Ciba-Geigy Corporation, Ardsley, N.Y.

[21] Appl. No.: 477,001

[22] Filed: Feb. 8, 1990

Related U.S. Application Data

[60] Division of Ser. No. 251,011, Sep. 27, 1988, Pat. No. 4,918,187, which is a continuation of Ser. No. 868,227, May 28, 1986, abandoned.

[51] Int. Cl.$^5$ .................................. C07D 281/18
[52] U.S. Cl. .................................. 540/454; 540/451; 540/491; 540/488; 540/500; 540/523; 540/526; 548/452; 548/492; 548/533; 548/537
[58] Field of Search ............ 540/451, 454, 491, 488, 540/500, 523, 526; 548/492, 452, 537, 533

[56] References Cited

U.S. PATENT DOCUMENTS 4,410,520 10/1983 Watthey .................... 540/523
4,473,575 9/1984 Watthey .................... 540/523
4,725,617 2/1988 Fodor et al. ............... 514/422

OTHER PUBLICATIONS

Morrison et al., Organic Chemistry 3rd Ed. (6/77).
Ben-Ishai et al., "Tetrahedron", vol. 33, pp. 1533-1542 (1977).
Meyer et al., "Journal of Organic Chem.", vol. 22, pp. 1560-1565 (1957).
Drugs of the Future, vol. 9, No. 5, pp. 317-319 (1984).
Slade et al., "Journal of Medicinal Chemistry", vol. 28: p. 1517 (1985).
Baumrucker et al., in "J Organic Chemistry", vol. 33, No. 10, Oct. 1968.

*Primary Examiner*—Robert T. Bond
*Attorney, Agent, or Firm*—Irving M. Fishman; JoAnn Villamizar

[57] ABSTRACT

The present invention relates to compounds of the formula

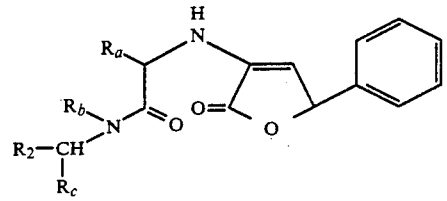

wherein
$R_c$ is carboxy, esterified carboxy or amidated carboxy;
$R_2$ is hydrogen or lower alkyl or joins with $R_a$ and $R_b$ and the atoms therebetween to form a fused ring

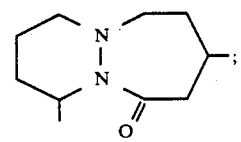

and either $R_a$ is methyl and $R_b$ is

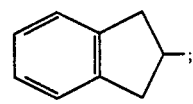

or $R_2$ and $R_b$ and the atoms therebetween form a group

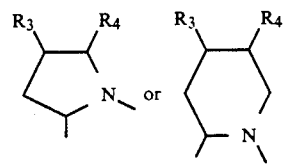

wherein $R_3$ and $R_4$ are either both hydrogen, or together are propylene, butylene, or with the two atoms to which they are attached form a benzene ring. Methods of manufacture and use thereof in the production of angiotensin converting enzyme inhibitors are disclosed.

4 Claims, No Drawings

(2,5-DIHYDRO 5-PHENYL-2-OXO-3-FURANYL)AMINES, METHODS OF MANUFACTURE, AND USE THEREOF IN THE PRODUCTION OF ANGIOTENSIN CONVERTING ENZYME INHIBITORS

This is a divisional of application Ser. No. 251,011, now U.S. Pat. No. 7,918,187 filed on Sep. 27, 1988 which is a continuation of application Ser. No. 868,227 field on May 28, 1986, now abandoned.

The invention relates to a novel process for the production of angiotensin converting enzyme inhibitors which uses cheaper starting materials, less toxic reagents, and allows for simple efficient and inexpensive diasterioisomer separation over the conventional synthetic means currently employed. Also within the scope of this invention are the novel [2,5-dihydro-2-oxo-5-phenyl-furan-3-yl]amine intermediates which make the process feasible and the method of their manufacture.

Heretofore, the angiotensin converting enzyme inhibitors, having a partial formula

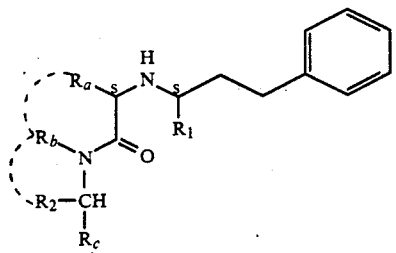

[A]

wherein the R groups are as defined below, have been prepared by via an expensive, time consuming, multi-step synthetic pathway requiring multiple purification steps which culminated in a Borsch Reduction and an extremely difficult diastereoisomeric separation. The details of such methods can be seen is U.S. Pat. Nos. 4,410,520 and 4,473,575. A specific synthetic pathway shown in the literature is given in Drugs of the Future, Vol. 9, No. 5, 1984.

It is an object of the invention to provide a synthetic pathway for the manufacture of angiotensin converting enzyme inhibitors (ACEI) and related compounds which is simpler and less costly than the known methods.

It is a further object of the invention to provide a synthetic pathway for ACEIs which allows for the rapid resolution of the product diastereoisomers.

It is another object of the invention to provide an ACEI synthetic pathway which avoids the use of many of the highly toxic reagents required in the known synthesis.

SUMMARY OF THE INVENTION

These and other important objects are attained by the instant invention which synthesizes the corresponding ACEI from 2-oxo-4-phenyl-trans-butenoic acid by condensation with an appropriate amine, $R_y\text{-NH}_2$, to result in the novel intermediate $N\text{-}R_y\text{-}[2,5\text{-dihydro-2-oxo-5-phenyl-furan-3-yl}]$amine. This compound is then hydrogenated whereby the furanyl ring becomes saturated, is opened, and the resulting hydroxy function on the benzyl moiety hydrogenated to result in a diastereomeric racemic mixture which can be separated into an essentially pure diastereomer (S,S) by slurrying or recrystallizing the product from acetonitrile.

While the invention is described mostly in terms of ACEI synthesis, the reaction mechanism is one of general applicability for obtaining a compound of the formula

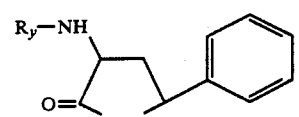

[B]

or

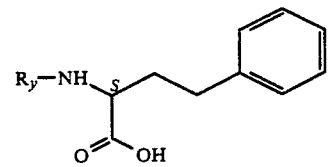

[C]

wherein $R_y$ is essentially any radical which will not interfere in the reaction $-\text{NH}_2+$

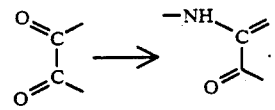

Compound C can be functionally modified by esterification or amidification as desired by means well known in the art.

DETAILED DESCRIPTION OF THE INVENTION

Angiotensin Converting Enzyme inhibitors [ACEI] are quickly becoming an important area of antihypertensive therapy. It is therefore crucial to develop more efficient, more economic, and safer ways to obtain these compounds. The instant invention provides just such a means.

The invention is a new method of producing an angiotensin converting enzyme inhibitor or precursor thereof of the formula

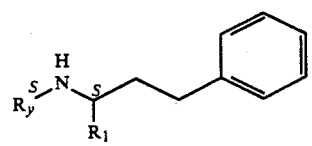

[D]

wherein $R_1$ is COOH, an esterified carboxy group or an amidated carboxy group. $R_y$, although it can be any organic radical in the generally applicable reaction, is essentially a group limited to the formula

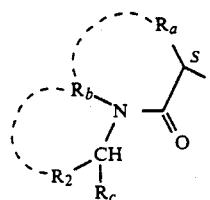

[E]

wherein $R_c$ is free carboxyl, esterified carboxyl, or amidated carboxyl; and a) $R_a$ is methyl or omega amino lower alkyl; $R_b$ is and $R_2$ is hydrogen or lower alkyl;

b) $R_a$ is methyl or omega amino lower alkyl; and $R_2$ and $R_b$ together along with the atoms to which they are attached form a group of the formula

[II] [IIa]

wherein n is 0 or 1, and $R_3$ and $R_4$ are each hydrogen or together with the two carbon atoms to which they are attached form a cyclopentane, cyclohexane, or benzene ring;

c) $R_2$, $R_a$, and $R_b$, together with the atoms therebetween, form a fused ring of the formula

[III]

d) $R_2$ is hydrogen or lower alkyl and $R_a$ and $R_b$, together with the atoms therebetween, form a group of the formula

[IV]

wherein m is 1 or 2;

X is O, S, SO, $SO_2$ or $CH_2$;

and $R_5$ and $R_6$ are each hydrogen, or together with the two carbon atoms to which they are attached form a benzene ring which is unsubstituted or mono or disubstituted by a substituent selected from lower alkyl, lower alkoxy, lower alkanoyloxy, hydroxy, halogen, or trifluoromethyl or the two substituents together are lower alkylenedioxy. The benzene ring formed by $R_5$ and $R_6$ may also be saturated so as to result in the cyclohexyl analogs. Whenever used, "lower" means up to 4 members.

Essentially, the method entails reacting an amine of the formula $R_y-\overset{S}{-}NH_2$ [F]

with β-keto-4-phenyl-but-3-ene-oic acid in the presence of an alcohol, preferably a lower alkanol, more preferably ethanol, to obtain a novel intermediate of the formula

[G]

These intermediates are also within the scope of the invention. A similar reaction using anilines instead of a compound of formula F is disclosed in J. Org. Chem. 33, No. 10, pp. 3991-3993 (1968).

The intermediate G is then catalylically hydrogenated, in the additional presence of an alcohol, preferably a lower alkanol, more preferably ethanol, to a compound of the formula

[H]

The hydrogenation reaction saturates the double bond in the 2,5-dihydro furan ring and causes the lactone bond to break, thereby opening the ring. Since this results in a benzylic hydroxy function, the hydrogenation continues so that the product of formula H is obtained. Although most any hydrogenation catalyst will suffice a Pd/C catalyst is especially preferred.

A surprising and important feature of the invention is that the resolution of the S,SR racemic mixture into the desired S,S compounds of formula D is simply and quickly accomplished by slurrying the mixture with or recrystallizing it from acetonitrile. The S,S diastereomer is generally obtained in greater than 98% optical purity.

When the desired end product (formula D) has $R_1$=COOH and the $R_c$ group is as desired in the starting material, the synthesis is complete. However, if $R_c$ was originally esterified or amidated and the desired product has $R_c$ as a free carboxyl group, reaction with HCl will yield the desired product. If the desired product is to have $R_c$ as an esterified or amidated group and $R_1$ as an esterified group, the desired $R_c$ group should be in the $R_y$—$NH_2$ compound. Then the product of the crystallization or slurrying step can be reacted with the desired alcohol, preferably a lower alkanol, most preferably ethanol, in the presence of $SOCl_2$ to yield the desired product. Further treatment of this product with about 4 N HCl at about 50° C. for about 1 hour will selectively free the $R_c$ carboxyl group without affecting the $R_1$ ester. Still further treatment with acid will free the $R_1$ carboxyl group as well.

Preferred esterification groups for the $R_1$ carboxyl group are pharmaceutically acceptable alcohols which esters may be cleaved under physiological conditions. In any case when the free $R_1$ carboxyl group is desired, any alcohol which is otherwise non reactive with the rest of the molecule and readily removable by known means is suitable as the esterification group for $R_1$. Lower alkanols are especially preferred, most especially ethanol.

In the case where the free $R_c$ carboxyl group is desired, any esterification and amidification group for the $R_c$ carboxyl group is suitable, provided it can be readily removed. In the case where $R_1$ is to remain esterified, any esterification or amidification group is suitable provided the $R_c$ ester or amide can be selectively removed vis-a-vie the $R_1$ ester group. When the $R_c$ carboxyl group is to remain esterified or amidated, these groups should be pharmaceutically acceptable. Preferably, the esters are of lower alkanols most suitably ethanol. Preferably, the amides are of ammonia, a lower alkyl amine or a di lower alkyl amine.

Preferred $R_y$ groups include

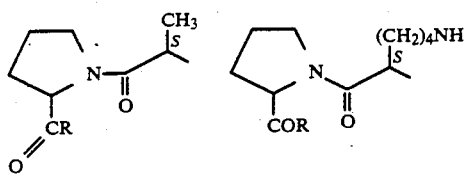

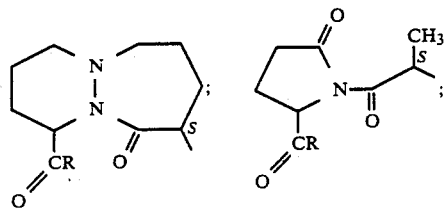

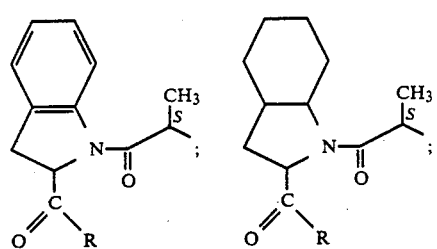

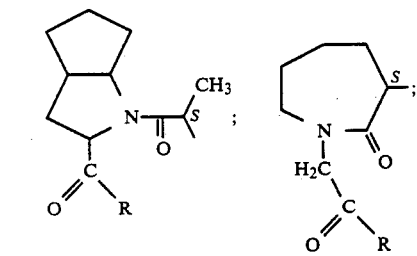

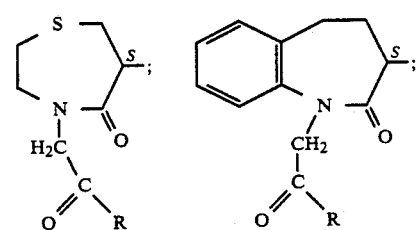

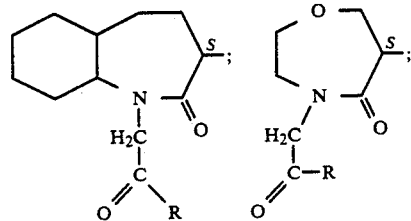

-continued

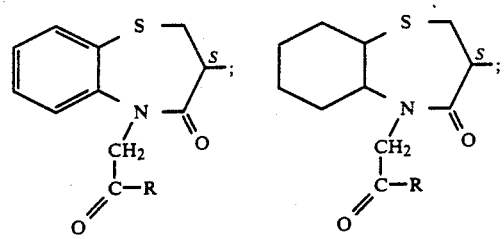

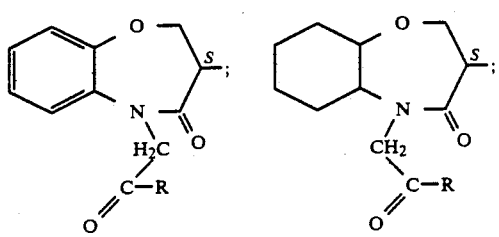

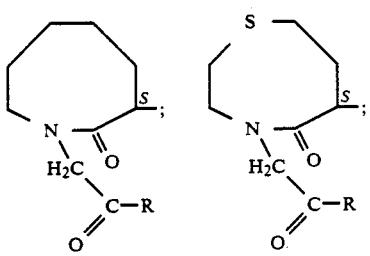

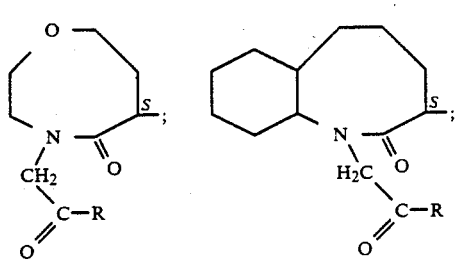

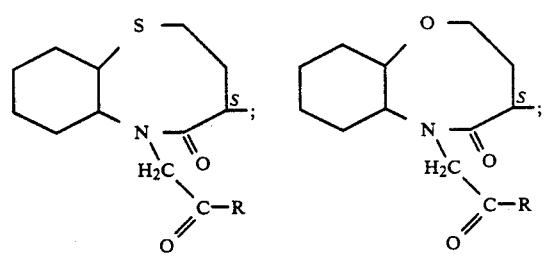

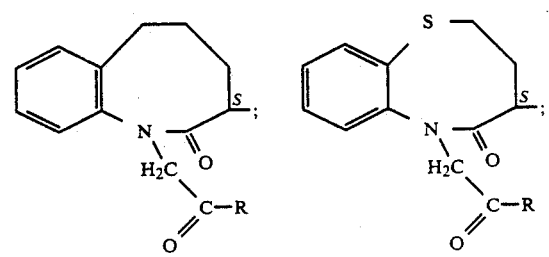

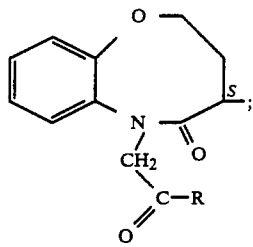

wherein R is OH, an ester group or an amide group. It is preferable that these ester and amide R groups be cleavable under physiological conditions and that they be derived from pharmaceutically acceptable alcohols and amines. However, where the R group is to be OH in the final product to be administered, other ester and amide groups are also suitable.

Most preferably the R group is OH.

Most preferably, the products of the instant process are of formula D wherein $R_1$ is COOH and $R_y$ is (enalapril)

(indalapril)

(indolopril)

(delapril) but $R_1$ is $CO_2C_2H_5$;

(quinapril) but $R_1$ is $CO_2C_2H_5$;

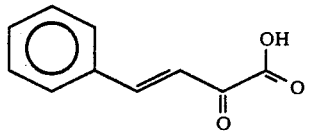 but $R_1$ is $CO_2C_2H_5$;

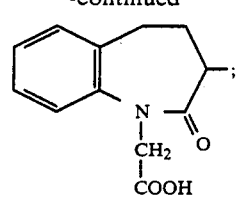

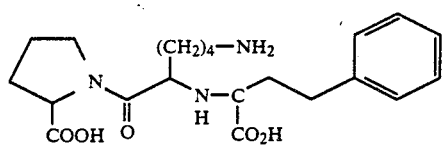 but $R_1$ is $CO_2C_2H_5$;

and the corresponding compounds of formula G above.

In addition to the above, lisinopril, having the formula

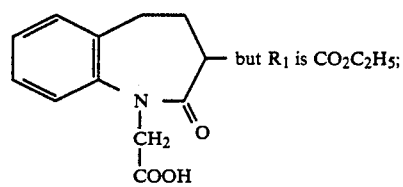

can also be made by the described process starting from

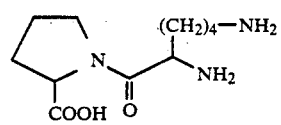

and

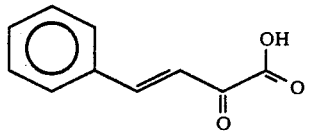 where the primary amine is suitably protected.

The invention will be more specifically understood in terms of the following examples, which are exemplary only and do not limit the scope of the invention.

EXAMPLE 1

Compound numbers in this Example are keyed to the reaction scheme set forth at the end of the Example.

Preparation of: Ethyl 3-[(2S dihydro-2-oxo-5-phenyl-5S-3-furanyl)amino]2345 tetrahydro 2 oxo 3S 1 benzazepine 1 acetate (compound 3)

To a solution of 0.935 g. (0.0055 moles) of 2 oxo-4 phenyl trans-3-butenoic acid in 8–10 mL of cold ethanol was added dropwise with stirring at 0° C. a solution of 1.3 g (0.005 moles) of Ethyl 3 amino-2,3,4,5-tetrahydro-2-oxo-13S) benzazepine 1-acetate. When the addition was complete the reaction mixture was stirred at 20° C. for 1 hour then allowed to warm to ambient temperature. After 20–48 hours the product precipitates out as a thick slurry and can be filtered to yield between 60–90% of the desired product depending on reaction time and temperature. m.p. 144–146° C. (crude). The product can be recrystalized — mp 146–148° C.

Preparation of Compound (4)

The unsaturated amino lactone compound 3 (25 g, 0.06 mol) was suspended in ethanol (1500 mL) and to this was added 4Å molecular sives (50 g) and 5 g of Pd/C 5%. The mixture was hydrogenated at ambient temperature for approximately 20 hours until the theoretical amount of hydrogen was consumed. The reaction mixture was filtered (to remove the catalyst and molecular sives) and the filter cake was washed with fresh ethanol (~1L). The combined filtrates were refiltered through celite and concentrated to yield 25 g of a white solid (crude product). The crude product was recrystalized from acetonitrile (~200 mL, 80° C.), and cooled to yield 8.3 grams (1st crop) of the SS diasteromer compound 4, mp. 185–186° C. Rot. $[\alpha]D^{25}$ 1% in Ethanol was ~ −156.87°.

Preparation of Compound 5 (the diester)

To a suspension of compound 4 [8.0 g (0.0188 mole) in ethanol (~80 mL) cooled to 6° C.]was added dropwise thionyl chloride 3.2 mL (4.88 g, 0.41 mol) to give a clear solution. The reaction mixture was refluxed for ~40 hours after which the reaction mixture was monitored by TLC (Tol: ETOAC: 1:1) and ETOAC, MEOH, NH4OH (17:3:3) and proved to be >90% complete. The reaction mixture was evaporated to dryness to yield the crude product which by HPLC analysis was >91% pure SS diasteromer of compound 5.

Preparation of Compound 6 (Alkaline conditions)

To a solution of diester 5 (1 g, 0.002 mol) in ethanol (10 mL) was added a solution of sodium carbonate (212 mg, 0.002, mol) in 8 mL of water followed by a solution of sodium hydroxide 1.8 mL of 1 M (0.0018 mol). The reaction mixture was stirred an ambient temperature and monitored by HPLC (C18 column, using a water →>methanol gradient over 20 minutes). When the reaction was complete, the ethanol was removed under vacuum and the aqueous residue was extracted 2 ×'s with diethyl ether (to remove any unreacted starting material) and the aqueous layer was then adjusted to a pH of 4.3 with 12N.HCl. The aqueous layer was extracted exhaustively with methylene chloride which were combined, dried (Na2SO4), and concentrated to yield ~400 mg (~46%) of the desired compound 6.

Preparation of Compound 6 (Acid conditions)

A suspension of the diester 5 (R=Et) (o.5 g, 0.01 mol) in 10 mL of 4 N. HCl was heated to 50° C. for about ~4 hours after which time the reaction mixture became homogenious and was monitored by HPLC (water/MEOH 25: 75) to yield > 88.5% of the desired product CGS 6. The reaction mixture was cooled and the product crystalized out of solution. The crystals were filtered and dried to yield the a crude product compound 6 which by HPLC was > 96% pure (impurities were ~1% diacid and 2% diester).

Preparation of compound 7

To a suspension of Compound 6 (1 g, 0.002 mol) in ethanol (about 10 mL) was added 4 mL of a 1.9 N solution of potassium hydroxide. The reaction mixture was stirred at ambient temperature for 1 hour, warmed to 50° C. for 10 minutes then cooled. The ethanol was removed under vacuum and the pH of the remaining aqueous solution was adjusted to pH 1 with 12 N-HCl and the desired product compound 7 precipitated out of solution. The product was filtered, washed with acetone, and dried to yield 600 mg product (mp. 278–280° C.).

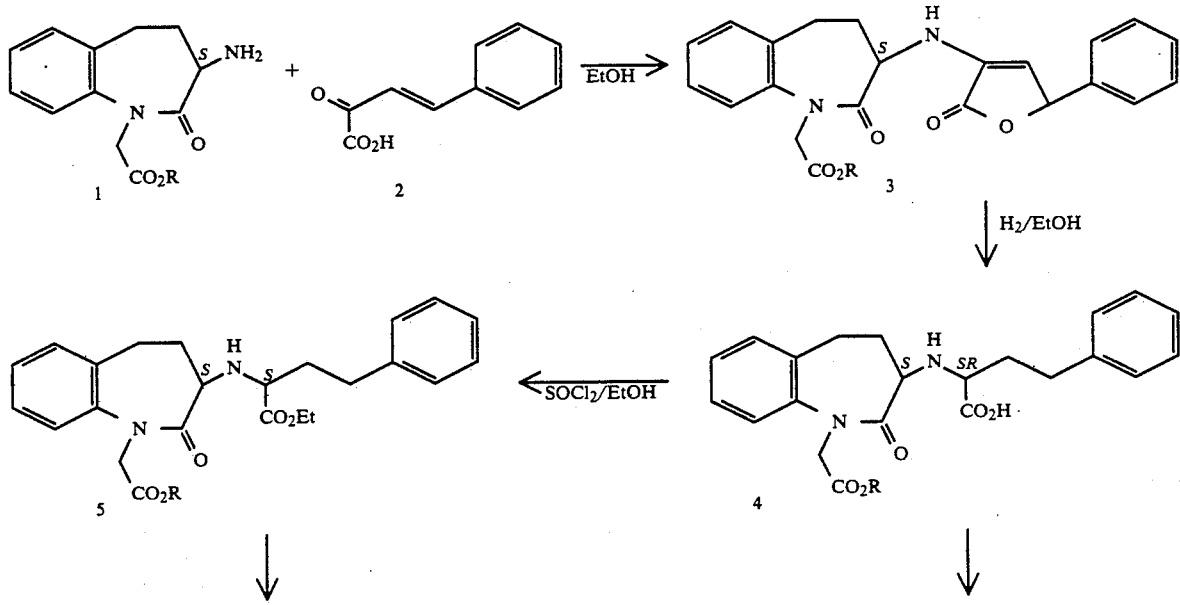

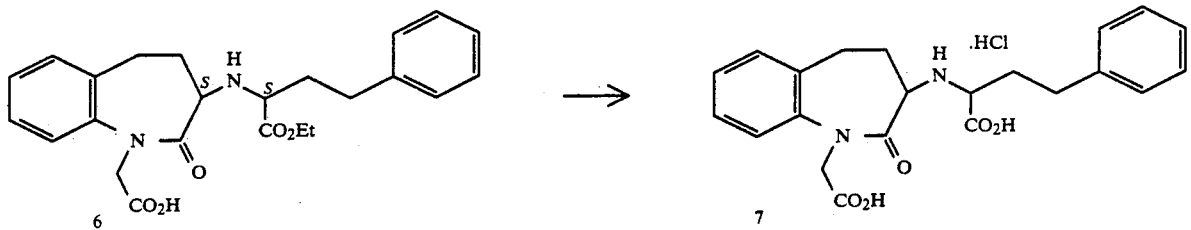

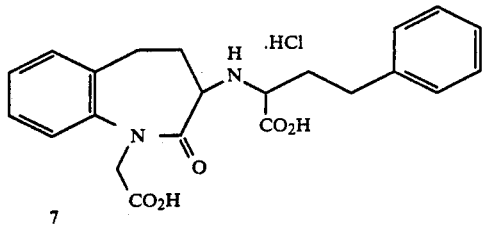

EXAMPLES 2–4

Example 1 was followed except that the R group in compound 1 was methyl, tert-butyl, and hydrogen respectively. In the case where R=hydrogen, hydrogenation of compound 3 and recrystallizing from acetonitrile yields compound 7 directly.

I claim:

1. A process for the manufacture of a compound of the formula

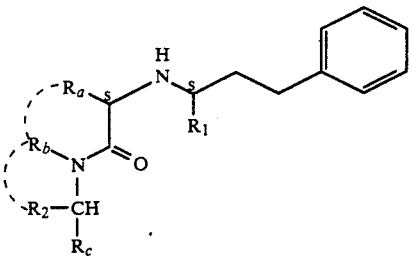

[I]

wherein a) $R_1$ and $R_c$ are each carboxyl-groups; $R_a$ is methyl or omega amino lower alkyl; $R_b$ is

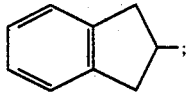

and $R_2$ is H or lower alkyl; or b) $R_1$ and $R_c$ are each carboxyl groups; $R_a$ is methyl or omega amino lower alkyl; and $R_2$ and $R_b$ together along with the carbon and nitrogen atoms to which they are attached form a group of the formula

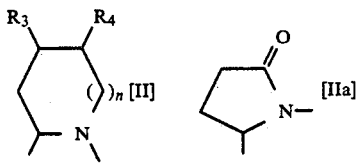

wherein n is 0 or 1; and $R_3$ and $R_4$ are each hydrogen, or together with the two carbon atoms to which they are attached form a cyclopentane, cyclohexane, or benzene ring; or c) $R_1$ and $R_c$ are each carboxyl; and $R_2$, $R_b$ and $R_a$ together with the atoms therebetween form a fused ring of the formula

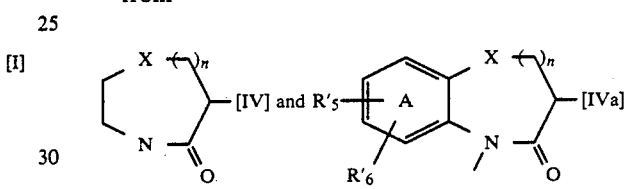

d) $R_1$ and $R_c$ are each carboxyl groups; $R_2$ is hydrogen or lower alkyl; and $R_a$ and $R_b$, together with the atoms therebetween form a group selected from

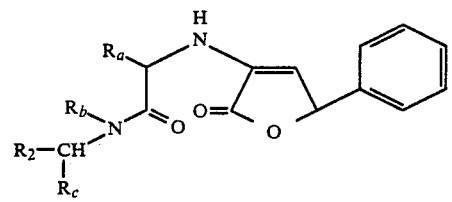

wherein $R_5$ and $R_6$ are each independently hydrogen, lower alkyl, lower alkoxy, lower alkanoyloxy, hydroxy, halogen, or trifluoromethyl, or $R'_5$ and $R'_6$ are together lower alkylenedioxy; X is O, S, $CH_2$, SO, $SO_2$; and n=1 or 2, comprising catalytically hydrogenating a compound of the formula

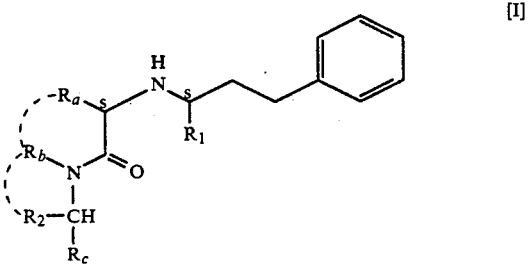

wherein $R_a$, $R_b$, $R_c$, and $R_2$ are as defined above in the presence of an alcohol, and recrystallizing from or slurrying with acetonitrile the product obtained from said hydrogenation to yield a compound of formula I.

2. A process for the manufacture of a compound of the formula

[I]

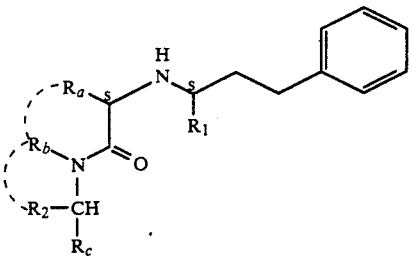

wherein

R₁ is a carboxyl group; R_c is an esterified or amidated carboxyl group; and a) R_a is methyl or omega amino lower alkyl; R_b is

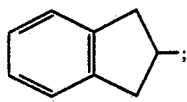

and R₂ is H or lower alkyl; or b) R_a is methyl or mega amino lower alkyl; and R₂ and R_b together along with the carbon and nitrogen atoms to which they are attached form a group of the formula

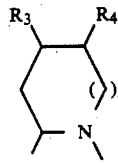 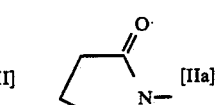

wherein n is 0 or 1; and R₃ and R₄ are each hydrogen, or together with the two carbon atoms to which they are attached form a cyclopentane, cyclohexane, or benzene ring; or c) R₂, R_b and R_a together with the atoms therebetween form a fused ring of the formula

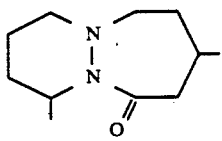

or d) R₂ is hydrogen or lower alkyl; and R_a and R_b, together with the atoms therebetween form a group selected from

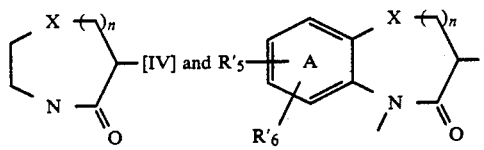

wherein R'₅ and R'₆ are each independently hydrogen, lower alkyl, lower alkoxy, lower alkanoyloxy, hydroxy, halogen, or trifluoromethyl, or R'₅ and R'₆ are together lower alkylenedioxy; X is O, S, CH₂, SO, SO₂; and m=1 or 2 comprising catalytically hydrogenating a compound of the formula

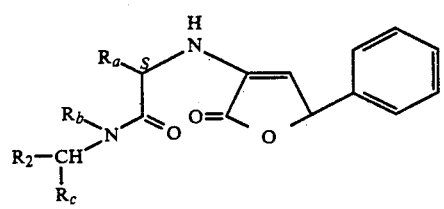

wherein R_a, R_b, R_c, and R₂ are as defined above in, the presence of an alcohol, and recrystallizing from or slurrying with acetonitrile the product obtained from said hydrogenation to yield a compound of said formula I.

3. The process of claim 1 wherein the group

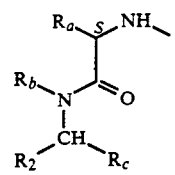

is selected from

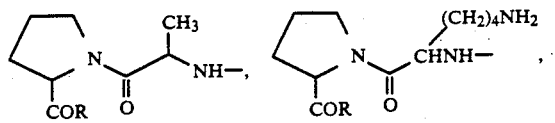

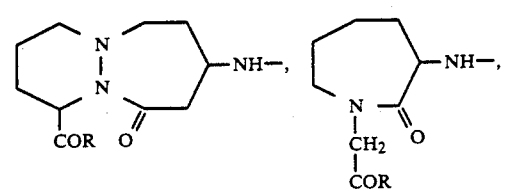

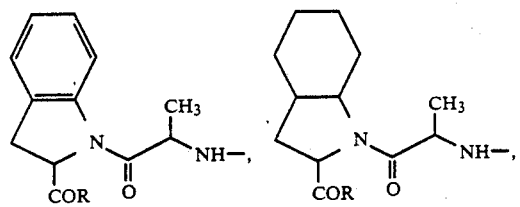

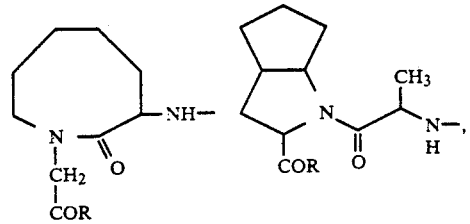

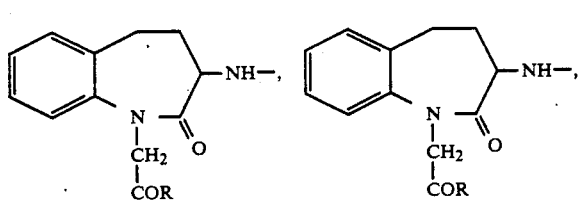

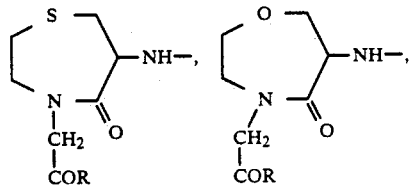

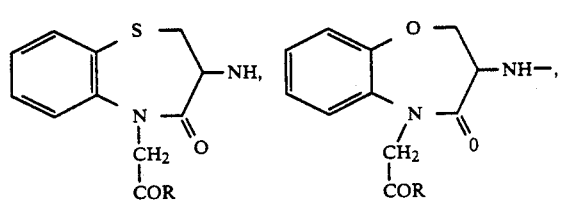

-continued
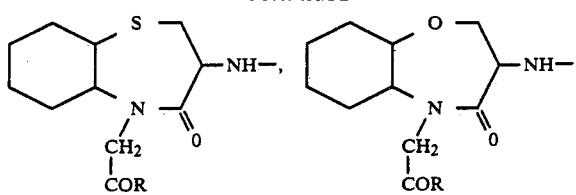
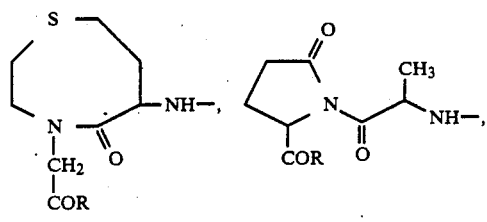
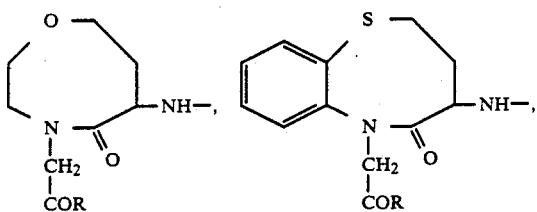
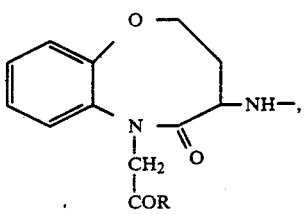
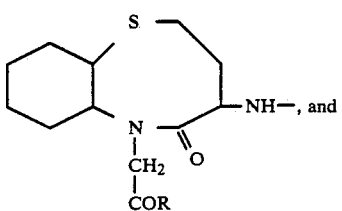
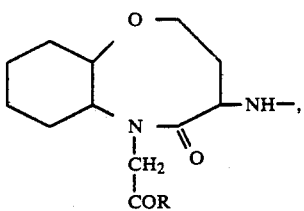
wherein COR is carboxy, esterified carboxy or amidated carboxy as defined in claim 1.
4. The process of claim 2, wherein the group
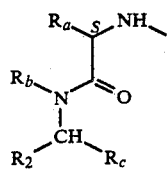
is selected from
-continued
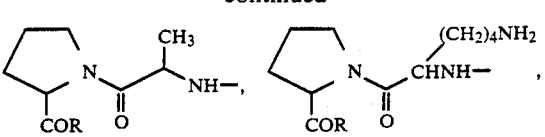
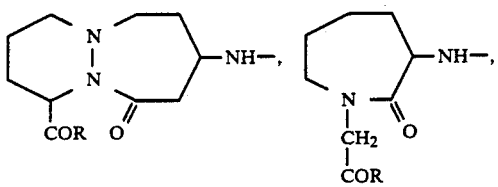
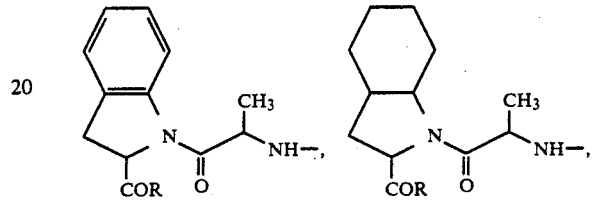
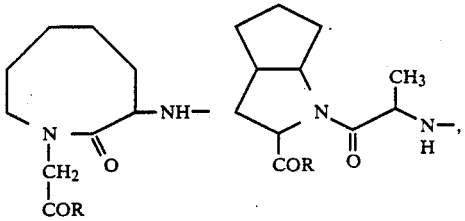
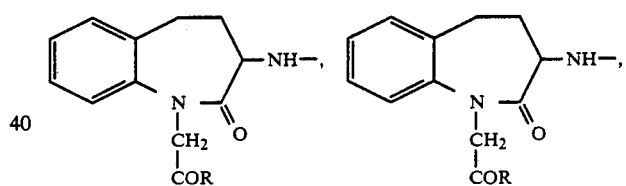
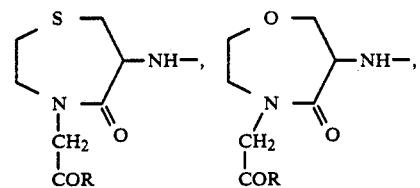
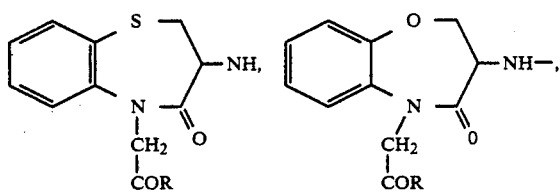
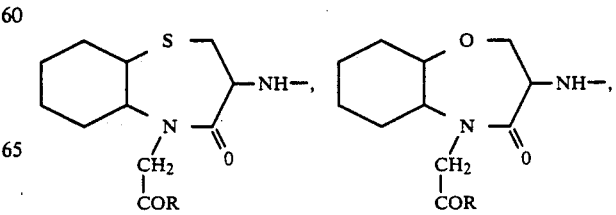

-continued
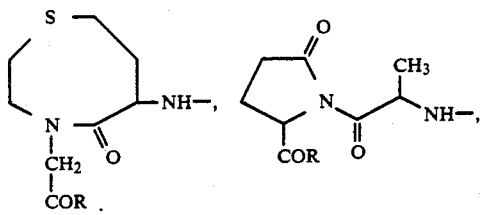
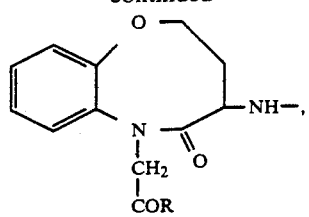
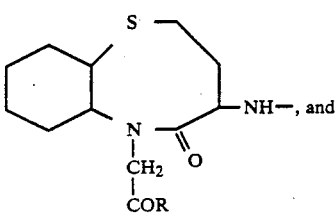
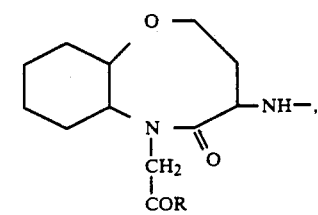
wherein COR is carboxy, esterified carboxy or amidated carboxy as defined in claim 2.
* * * * *